United States Patent
Morgan

(10) Patent No.: US 6,295,475 B1
(45) Date of Patent: Sep. 25, 2001

(54) SINGLE-PASS ATRIAL VENTRICULAR LEAD WITH MULTIPLE ATRIAL RING ELECTRODES AND A SELECTIVE ATRIAL ELECTRODE ADAPTOR FOR THE CORONARY SINUS REGION

(75) Inventor: Kevin L. Morgan, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/428,622

(22) Filed: Oct. 27, 1999

(51) Int. Cl.[7] ........................................ A61N 1/09
(52) U.S. Cl. ............................................. 607/122
(58) Field of Search .............................. 607/38, 119, 122, 607/123, 124, 148

*Primary Examiner*—William E. Kamm

(57) ABSTRACT

An implantable cardiac device having a control unit and a single-pass lead adapted to be implanted within the coronary sinus region so as to provide therapeutic electrical stimulation, such as stimulation pulses, to the left atrium and the left ventricle. The single-pass lead includes a ventricular electrode and a plurality of atrial electrodes spaced along the lead. One of the atrial electrodes can be selected as the atrial pacing electrode by manipulating a connector that interconnects the single-pass lead to the control unit. In one embodiment, a pacing electrode/sensing electrode combination can be selected by manipulating a connector that interconnects the single-pass lead to the control unit.

22 Claims, 11 Drawing Sheets

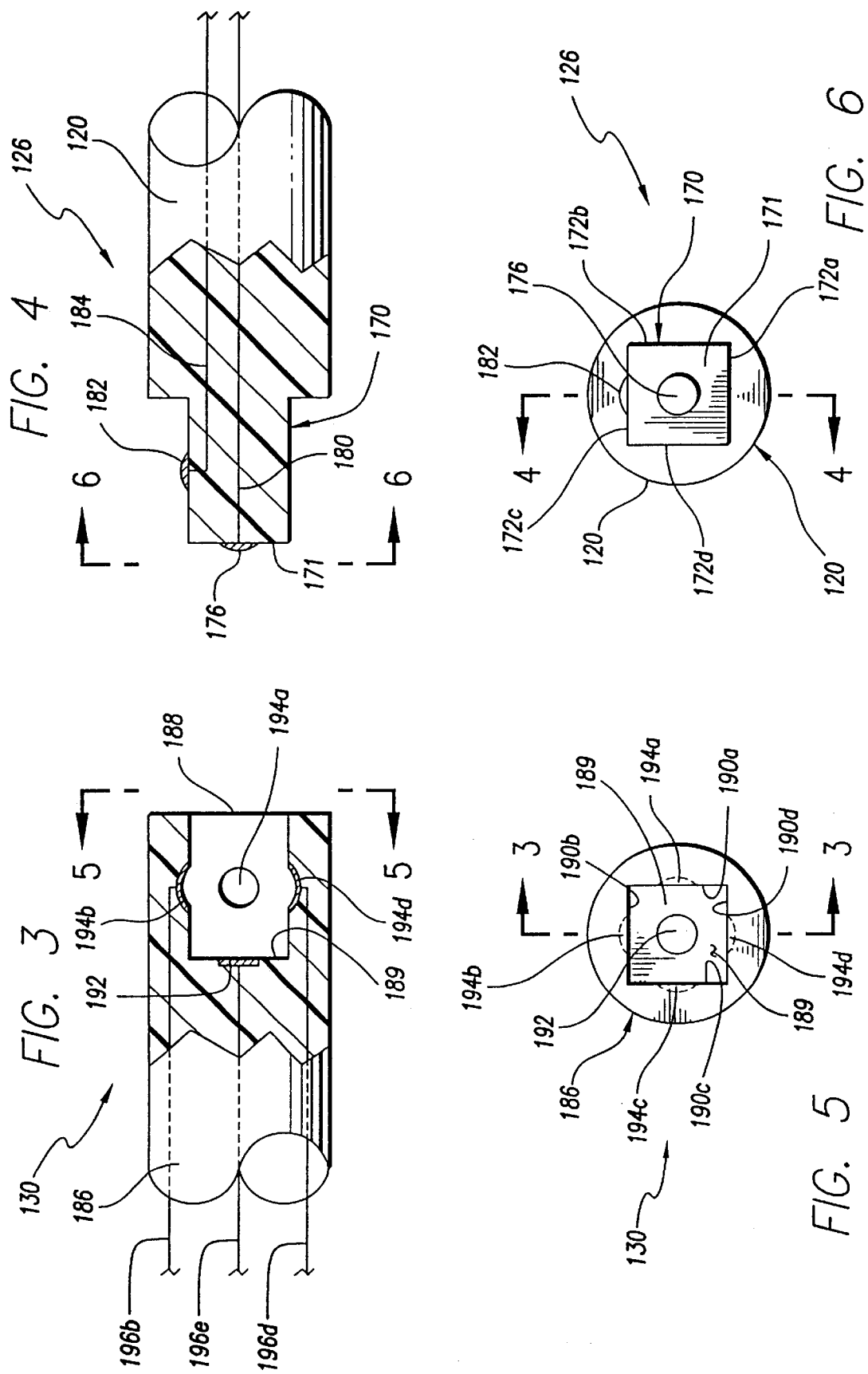

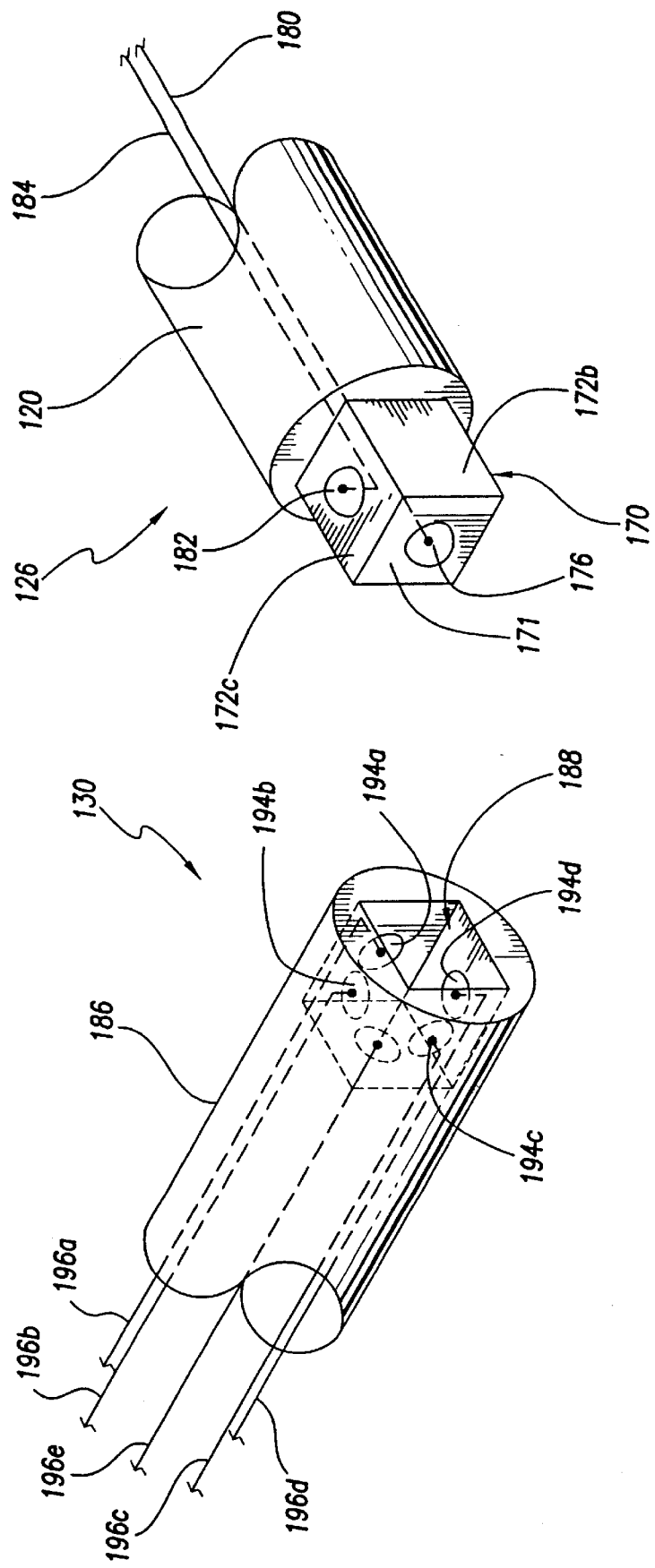

| BIPOLAR | | |
|---|---|---|
| PACE | – | SENSE |
| 156a | – | 156b |
| 156b | – | 156c |
| 156c | – | 156d |
| 156d | – | 156e |
| 156e | – | 156a |

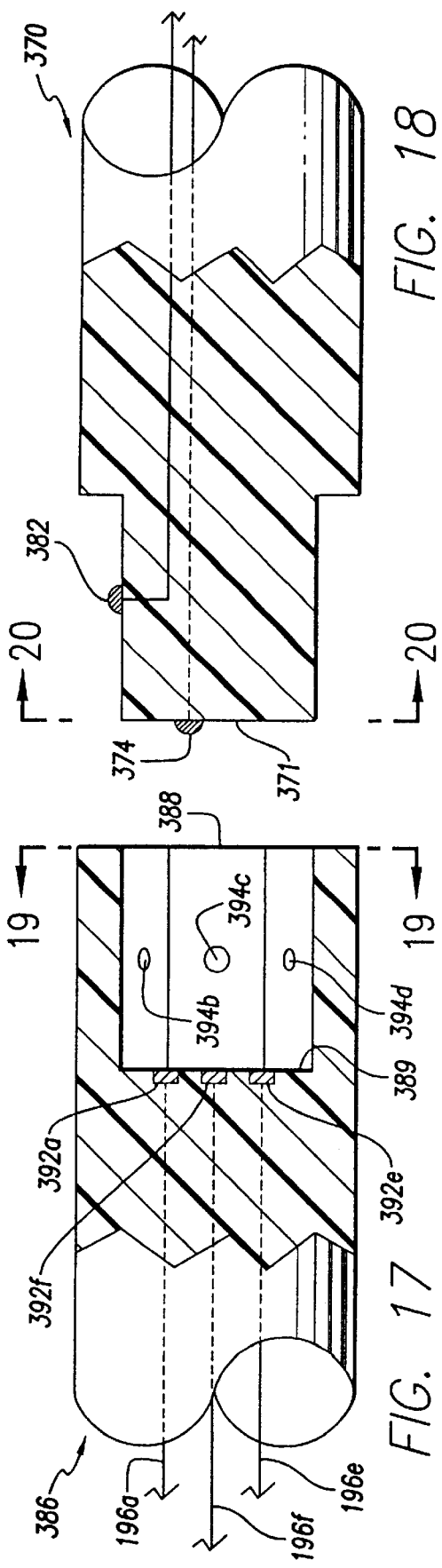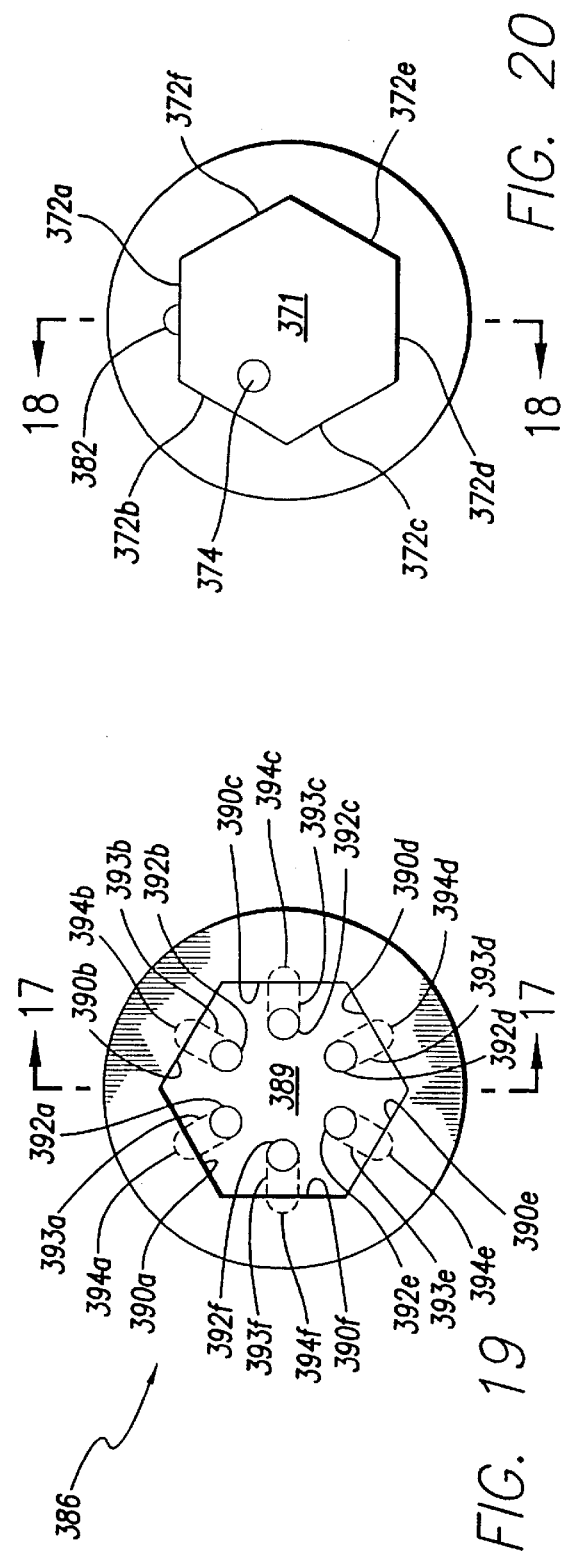

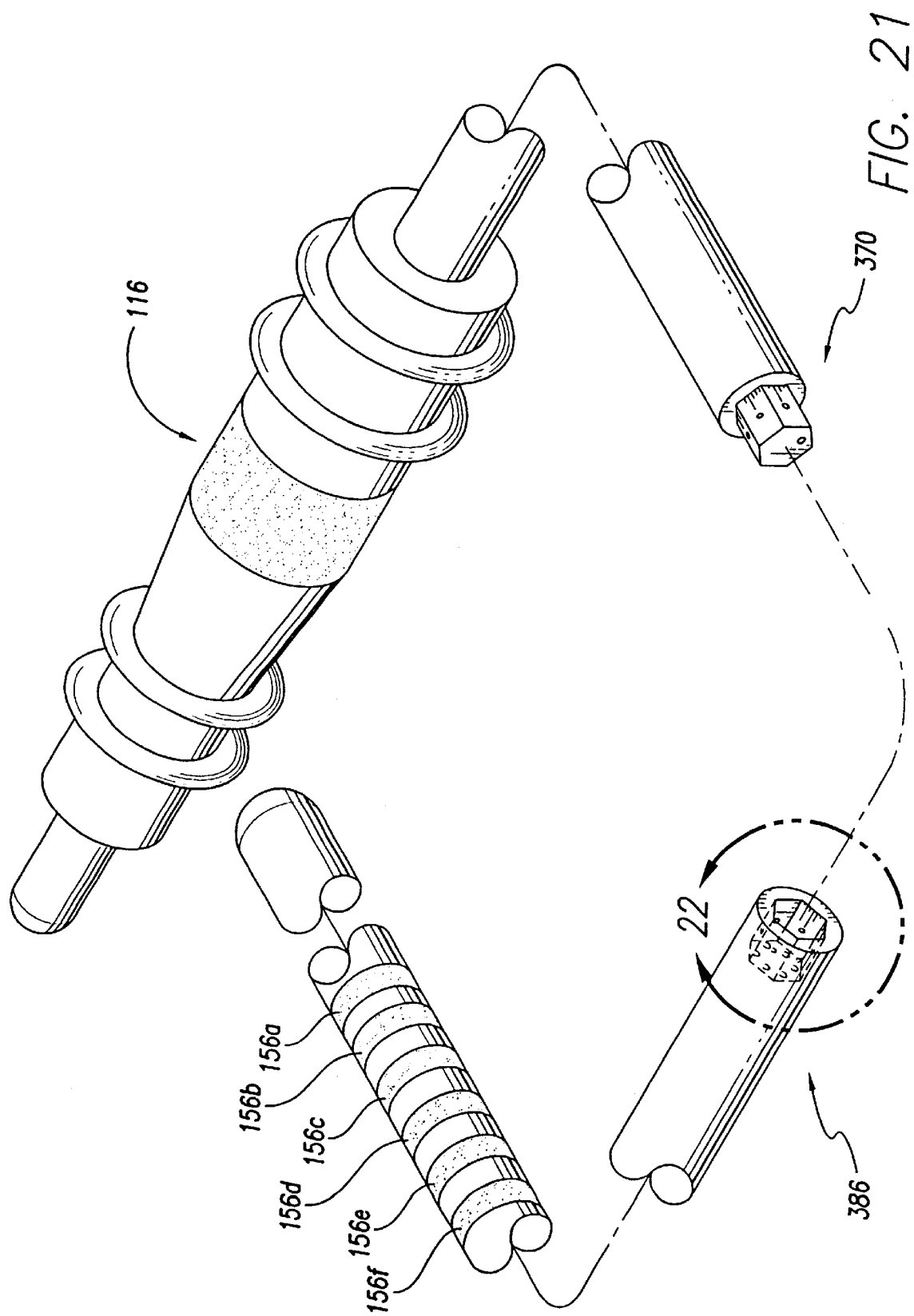

SINGLE-PASS ATRIAL VENTRICULAR LEAD WITH MULTIPLE ATRIAL RING ELECTRODES AND A SELECTIVE ATRIAL ELECTRODE ADAPTOR FOR THE CORONARY SINUS REGION

FIELD OF THE INVENTION

The present invention relates to implantable cardiac stimulating devices and, in particular, relates to a pacemaker lead adapted for pacing the left atrium and the left ventricle via a lead implanted within the coronary sinus region of the heart.

BACKGROUND OF THE INVENTION

Implantable cardiac devices are commonly used for treating patients with heart arrhythmias. These devices include well-known pacemakers and implantable cardioverter-defibrillators (ICD's). In general, these devices include a lead that is adapted to be implanted in the body of the patient so as to be positioned adjacent the heart and a control unit that is also adapted to be implanted within the patient which is connected to the lead so as to deliver electrical impulses to the heart via the lead. Pacemaker devices can be very sophisticated and include sensors and processing capabilities so that pacing is provided only when needed.

In pacing applications, the lead is typically implanted within the chambers of the heart so as to be positioned adjacent the walls of the right atrium or the right ventricle. In many typical pacemakers, the leads are implanted so that the lead is positioned within the right atrium and the right ventricle chambers so that a pacing pulse can be delivered directly to cardiac cells of these chambers to induce a paced response of the heart.

There are several different types of leads that are currently in common use in pacing applications. One very common lead is a bipolar lead which includes a pacing electrode and a sensing electrode. The pacing pulse is delivered to the cardiac cells by the pacing electrode and the sensing electrode serves as the return path for the pacing pulse. Typically, the sensing electrode is also configured so as to monitor intrinsic heart activity and provide a signal indicative thereof to the control unit. Other types of leads include unipolar leads which have a single electrode for delivering stimulation pulses to the heart and an indifferent electrode, such as the casing of the control unit, serves as the return electrode for the stimulation pulses.

As discussed above, pacemaker electrodes are typically implanted within the right atrium and right ventricle. The right atrium and the right ventricle generally provide blood circulation to the pulmonary system, i.e., circulation to the heart itself. The left atrium and the left ventricle provide circulation to the rest of the body's circulatory system including the major organs of the body such as the brain. Typically, implantation within the right atrium and the right ventricle has been preferred to implanting leads within the left atrium and the left ventricle has generally been thought to be too invasive of a procedure and to pose undesirable risks of complications to the flow of blood in the circulatory system. However, as the blood in the circulatory system is primarily pumped by the left atrium and the left ventricle, pacing the right atrium and the right ventricle may not always provide optimum results in ensuring adequate circulation of blood in the circulatory system. In some circumstances, right atrium and right ventricle pacing does not ensure that the major organs of the circulatory system, including the brain, receive adequate blood flow.

Consequently, there has been a desire to develop techniques for directly pacing the left atrium and the left ventricle. One such technique involves the implantation of leads through the right atrium into the coronary sinus region. As used herein, the phrase "coronary sinus region" refers to the coronary sinus vein, great cardiac vein, left marginal vein, left posterior ventricular vein, middle cardiac vein, and/or small cardiac vein or any other cardiac vein accessible by the coronary sinus.

The coronary sinus is a vein in the coronary circulatory system that is typically located in the heart so as to be proximal the outer walls of the left atrium and left ventricle of the heart. The coronary sinus vein has an opening in the right atrium that is accessible for lead implantation. By implanting a lead within the coronary sinus region and then positioning the lead so that the lead electrodes are adjacent the left atrium or the left ventricle, it is thought that stimulation pulses can be provided to the left atrium or the left ventricle. This allows these chambers to be paced without the complications associated with directly implanting leads in these chambers.

However, there are several problems which have limited the utility of left atrium, left ventricle pacing using leads implanted within the coronary sinus region. Currently contemplated techniques for pacing the left side of the heart involve implanting a dedicated atrial lead and electrode or a dedicated ventricular lead and electrode. However, current lead designs do not facilitate implanting leads to pace both the left atrium and the left ventricle. As the leads are to be implanted within the coronary sinus region and other pulmonary veins, it is often not possible to effectively position multiple sets of leads within the confined spaces of these veins and still allow for adequate blood flow within these veins.

One possible solution to this problem is to use a single-pass lead that incorporates both the ventricular pacing and sense electrodes and separate atrial pacing and sense electrodes. The atrial and ventricular electrodes are spaced apart a set distance so that each pair of electrodes can be positioned in the coronary veins where the electrode pairs could pace the left atrium or left ventricle, respectively. However, a single lead incorporating both left atrial pacing electrodes and left ventricular pacing electrodes that are separated by a fixed distance may not result in the atrial or ventricular electrodes being positioned in the location that is best adapted for delivery of stimulation pulses to the heart of a given patient. This may be the result of either different patients having different sized hearts or the response of the hearts of different patients to stimulation pulses varying depending upon where the pacing pulse is delivered.

Moreover, implanting leads within the coronary sinus region can be a time-consuming and invasive procedure. It may not be possible for the implanting physician to be able to precisely locate both the atrial electrodes and the ventricular electrodes in the coronary venous system to provide the optimum pacing for the patient in an efficient manner.

This is especially true for leads having atrial electrodes and ventricular electrodes spaced apart a set distance. Positioning the ventricular electrode in the optimum position for pacing the left ventricle may result in the atrial electrode being positioned where it is unable to provide effective pacing for the left atrium. Moreover, the implanting physician will not generally be able to ascertain the best location for each of the electrodes until the lead is implanted. Hence, the implanting physician may have to repeatedly implant leads and then remove and replace the implanted lead with a lead that has a different separation between the atrial electrodes and the ventricular electrodes. This process may significantly increase the length and invasiveness of the implantation procedure.

Hence, there is a need for a pacing lead system that is adapted to be efficiently implanted within the coronary veins so as to be able to deliver stimulation pulses to both the left atrium and the left ventricle of the patient's heart. To this end, there is a need for a lead which will allow the treating physician to implant a lead that occupies a limited amount of space within the coronary veins, but allows the implanting physician the flexibility of being able to locate the electrodes within the coronary venous system so as to optimize the delivery of stimulation pulses to the patient.

SUMMARY OF THE INVENTION

The aforementioned needs are satisfied by the lead of the present invention which includes a lead body adapted to be implanted within the coronary sinus region of the patient so as to be adjacent the left atrium or left ventricle of the heart and a plurality of electrodes spaced along a portion of the lead body so that when the lead body is implanted at least one of the plurality of electrodes can deliver stimulation pulses to the patient's heart to stimulate a chamber of the heart from the coronary veins. In one aspect of the invention, the lead body can be configured to selectively connect one of the electrodes to a control unit so that the selected electrode provides the therapeutic electrical stimulations to the chamber of the heart.

In one embodiment, the lead includes a ventricular pacing electrode located adjacent a first end of the lead body that is adapted for delivering stimulation pulses to the left ventricle of the heart. In this embodiment, the lead also includes a plurality of atrial electrodes that are spaced along the lead body so that when the lead body is implanted within the coronary veins with the ventricular electrode positioned to deliver stimulation pulses to stimulate the left ventricle, at least one of the atrial electrodes is positioned at a location within the coronary sinus region so that the at least one atrial electrodes can provide stimulation pulses to stimulate the left atrium. The lead body is preferably selectable so that the at least one atrial electrode can be selected as the electrode that will provide the stimulation pulses to the left atrium.

In one embodiment, the lead includes a connector that connects the lead body to an implanted control unit that produces the stimulation pulses. The connector can preferably be connected in a plurality of different connector configurations wherein in each connector configuration a different atrial electrode is coupled with the control unit so as to be able to deliver the stimulation pulses to the left atrium of the patient. In one particular embodiment, the connector includes a proximal connector and a distal connector that are to be connected together, wherein the proximal connector has a first shape having a first face wherein a pacing contact is positioned on the first face and the pacing contact is connected to the control unit. In this embodiment, the distal connector defines a plurality of faces each having a contact that is electrically connected to one of the atrial electrodes. The proximal and distal connectors are further configured so that the first face of the proximal connector can be positioned adjacent each of the different faces of the distal connector so that the control unit can be electrically connected to each of the plurality of atrial electrodes.

In one particular embodiment, the proximal connector is comprised of a geometrically shaped post having a plurality of faces and the distal connector is comprised of a geometrically shaped recess having a plurality of faces adapted to receive the geometrically shaped post such that the faces of the geometrically shaped post are positioned adjacent the faces of the geometrically shaped recess. In this embodiment, a single face of the proximal connector includes the pacing contact and a plurality of the faces of the distal connector contain the atrial electrode contacts so that the pacing contact can be selectively connected to the atrial electrodes.

The present invention therefore allows an implanting physician to implant the lead within the coronary venous system and, once the lead is implanted, select the atrial electrode from the plurality of atrial electrodes distributed through the coronary veins that will provide the optimum pacing of the heart from the coronary venous system. The selection, in one embodiment, can be accomplished based upon the manner in which the lead is connected to the control unit as the lead preferably includes a connector having multiple connection configurations that will allow selective electrical connection to a plurality of atrial electrodes to the control unit. These and other objects and advantages will become more apparent from the following discussion taken in conjunction with the accompanying drawings.

BRIEF DESCRIPTION OF THE DRAWINGS

FIGS. 3 and 4 show a cross-sectional view of a first embodiment of the proximal and distal connectors that determine which combination of electrodes will be used for pacing and sensing;

FIG. 5 is an end view of the distal connector shown in FIG. 3;

FIG. 6 is an end view of the proximal connector shown in FIG. 4;

FIG. 7 is an isometric illustration of the distal connector shown in FIG. 3;

FIG. 8 is an isometric illustration of the proximal connector shown in FIG. 4;

FIGS. 17 and 18 illustrate another embodiment for a proximal and distal connector that determine which combination of electrodes will be used for pacing and sensing;

FIG. 19 is an end view of the distal connector shown in FIG. 17;

FIG. 20 is an end view of the proximal connector shown in FIG. 18;

FIG. 21 is an isometric illustration of the lead assembly shown in FIGS. 17 and 18;

DETAILED DESCRIPTION OF THE PREFERRED EMBODIMENT

Reference will now be made to the drawings wherein like numerals refer to like parts throughout.

Figure 1:
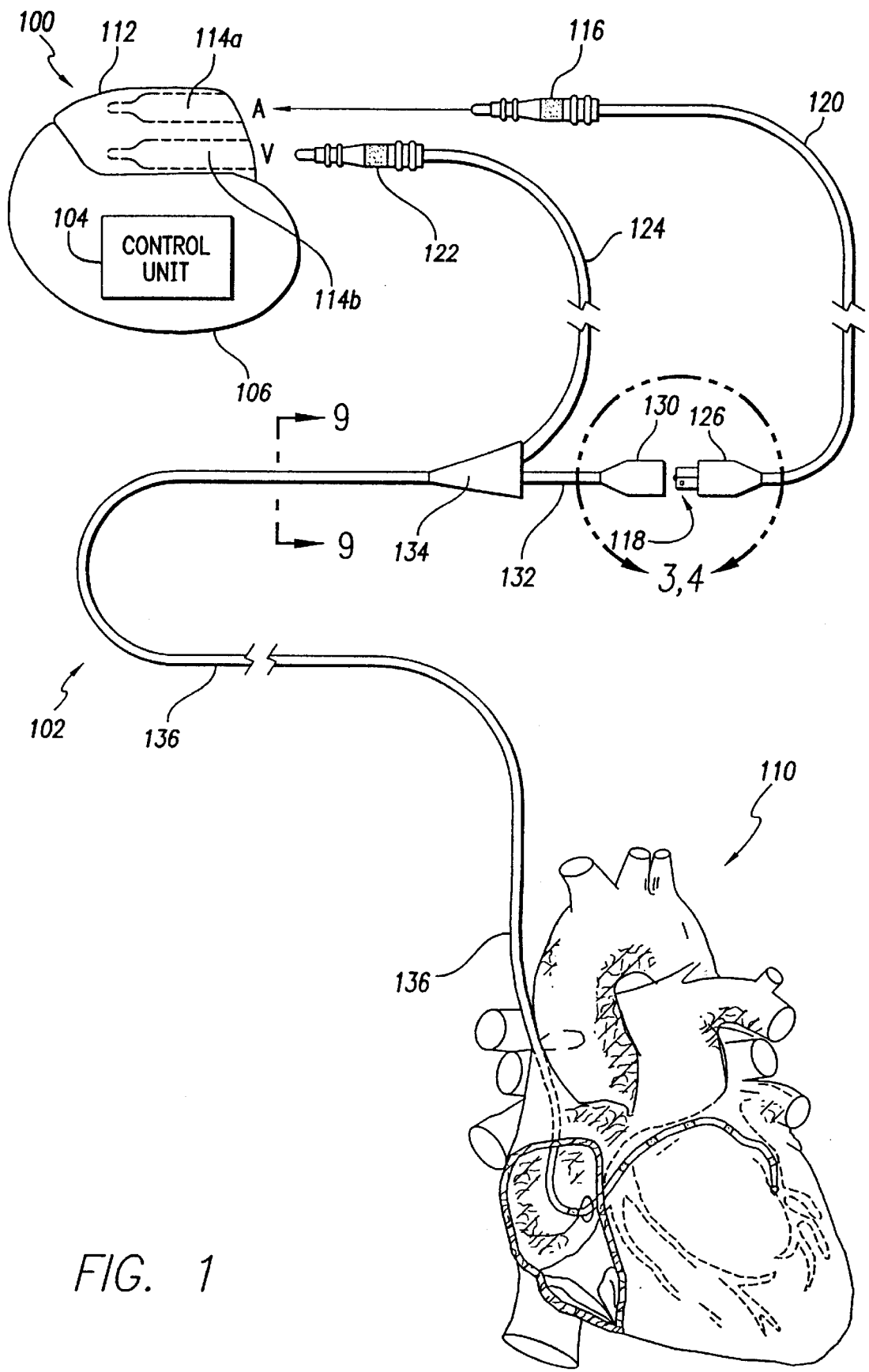
FIG. 1 is a diagram illustrating the components of an implantable cardiac device of the preferred embodiment incorporating a single-pass lead with multiple atrial ring electrodes as it is implanted within the heart.

FIG. 1 illustrates an implantable cardiac device 100 that incorporates a lead 102 and a control unit 104. The control unit 104 is positioned within a casing 106 and contains electronic circuitry for controlling the delivery of therapeutic electrical stimulation, such as stimulation pulses, to the heart 110 of the patient via the lead 102. In particular, the control unit 104 includes a processor, pacing pulse generation and delivery circuits and a sensing circuit that receive signals indicative of the function of the heart from electrodes that are part of the lead 102. The components of the control unit 104 are preferably well known components that function in a manner known in the art.

In this embodiment, the casing 106 also includes a pacemaker header 112 that, in this embodiment, conforms to the well known IS-1 standard. The pacemaker header 112 includes an opening 114a that is adapted to receive and secure a connector 116 for a proximal atrial lead body 120 in a well known manner. Similarly, the header 112 also includes an opening 114b that is adapted to receive a connector 122 that is attached to a proximal ventricular lead body 124 in a well known manner. As will be described in greater detail below, the proximal atrial lead body 120 includes a pacing and sensing conductor that will be coupled to the atrial pacing and sensing electrodes of the portion of the lead 102 that is implanted within the coronary sinus region of the heart 110 near the right and/or left atrium. Similarly, the proximal ventricular lead body 124 also includes conductors that are adapted to connect to the ventricular pacing and ventricular sensing electrodes of the portion of the lead 102 that is implanted deep within the coronary sinus region of the heart 110 so as to stimulate the left ventricle.

As illustrated in FIG. 1, the proximal atrial lead body 120 includes a proximal connector 126 that engages with a distal connector 130 that is attached to a distal atrial lead body 132 so as to form a connection 118. As will be described in greater detail below, the proximal connector 126 and the distal connector 130 can be connected together in a plurality of connection configurations which result in a different atrial electrode being electrically coupled to the control unit 104. Both the proximal ventricular lead body 124 and the distal atrial lead body 132 enter a junction 134 which is connected to a distal single-pass lead body 136. The distal single-pass lead body 136, in one embodiment, is a lead body comprised of silicon rubber tubing that has a plurality of lumens which are adapted to carry electrical conductors to a plurality of electrodes mounted on the lead body 136 so as to be positioned in the coronary sinus region of the heart 110 when the lead body 136 is implanted as will be described in greater detail below.

Figure 2:
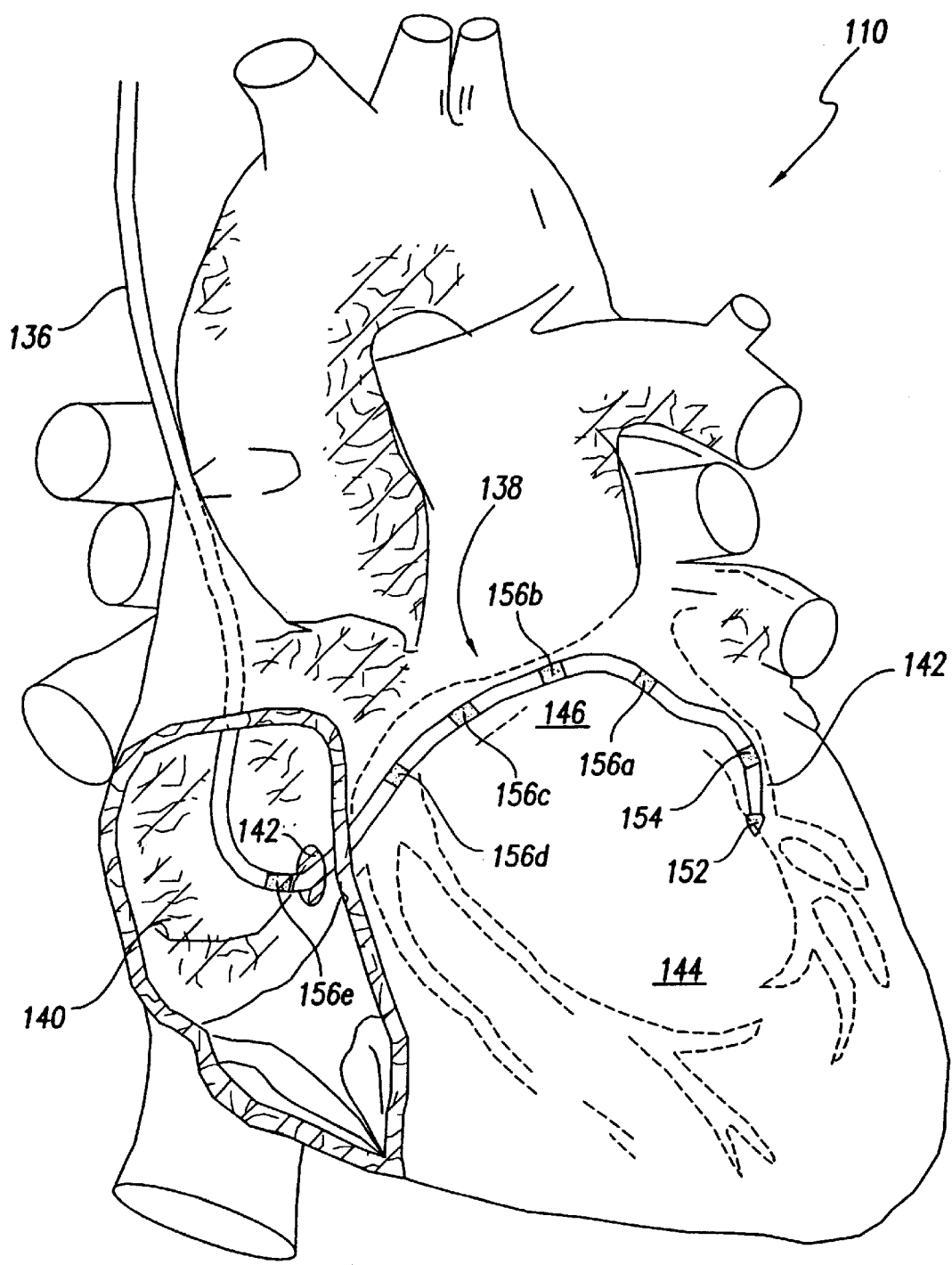
FIG. 2 is an enlarged view of the distal end of the lead of FIG. 1 illustrating the positioning of the atrial ring electrodes in the coronary venous system of the heart.

FIG. 2 illustrates the configuration of the portion 138 of the distal single-pass lead body 136 that is adapted to be implanted within the coronary sinus region of the patient's heart 110. The implanted portion 138 includes a ventricular tip electrode 152 of a type known in the art that is positioned at the very distal tip of the distal single-pass lead body 136. A ventricular ring electrode 154 in the shape of a ring is positioned a first distance from the tip electrode 152. The ventricular ring electrode 154 is electrically connected to the control unit 104 so as to serve as both a return path for a ventricular pacing pulse delivered by the ventricular tip electrode 152 and also to provide a bipolar sense signal to the control unit 104 indicative of the activity of the heart. The configuration and operation of the ventricular tip electrode 152 and the ventricular ring electrode 154 are substantially the same as ventricular tip electrodes and ring electrodes known in the art.

As illustrated in FIG. 2, the implanted portion 138 of the distal single-pass lead body 136 is passed through the coronary os 142 and positioned in the coronary sinus region so that the ventricular tip electrode 152 and the ventricular ring electrode 154 are positioned at a location substantially adjacent the left ventricle 144 of the heart. By positioning the ventricular tip electrode 152 and the ring electrode 154 in this location within the coronary sinus region, the control unit 104 can be adapted to deliver stimulation pulses so as to pace the left ventricle 144 without requiring the electrodes be implanted deep within the left ventricular chamber 144.

As is also illustrated in FIG. 2, the implanted portion 138 of the distal single-pass lead body 136 also includes a plurality of atrial electrodes 156a–156e, which, in this embodiment, are well-known ring electrodes. The atrial ring electrodes 156a–156e are spaced along the implanted portion 138 of the distal single-pass lead body 136 so that at least some of the plurality of atrial ring electrodes 156a–156e are distributed within the coronary sinus region so as to be spaced along a region adjacent right and/or the left atrium 146 of the heart 110. In this embodiment, the plurality of atrial ring electrodes 156a–156e includes an atrial ring electrode 156e that is actually positioned in the right atrium 140 to thereby also allow right atrial pacing.

Hence, the implanted portion 138 of the distal single-pass lead body 136 has a plurality of atrial electrodes 156a–156e, that, when the implanted portion 138 is positioned within the coronary sinus region, are distributed over a region of the heart in a plurality of different positions with respect to the left atrium 146. As will be discussed in greater detail below, the implanting physician will be able to select one of the atrial electrodes 156 to function as the left atrial pacing electrode thereby allowing the implanting physician to select the atrial electrode 156 which provides the most optimum pacing performance for the particular patient. This allows the implanting physician to use a single-pass lead to provide both left atrial and left ventricular pacing.

Moreover, because there is a single ventricular pacing electrode and a distributed plurality of potential atrial pacing electrodes, the implanting physician can focus their implantation technique on ensuring that the ventricular electrode 152 is implanted in the desired location within the coronary sinus region so as to provide optimal pacing to the left ventricle 144 of the heart 110. Once the ventricular pacing electrode 152 is correctly positioned, the plurality of atrial electrodes 156 will be distributed along the implanted portion 138 of the single-pass lead body 136 in the coronary sinus region so that preferably at least one of the atrial electrodes 156 is positioned within the coronary sinus region in a location that will facilitate right and/or left atrial pacing.

The implanting physician then has to select the atrial electrode 156 that provides the most optimum pacing to the right and/or left atrium in the manner that will be described in greater detail below.

In this embodiment, the manner in which the implanting physician selects that atrial pacing electrode from the plurality of electrodes 156a–156e, is dependent upon the manner in which the implanting physician interconnects the proximal atrial connector 126 (FIG. 1) with the distal atrial connector 130 (FIG. 1).

FIGS. 3 and 4 show a cross-sectional view of a first embodiment of the distal connector 130 and the proximal connector 126, respectively, that determine which combination of electrodes will be used for pacing and sensing. FIGS. 5 and 6 illustrate an end view, and FIGS. 7 and 8 illustrate an isometric view, of the distal connector 130 and the proximal connector 126 shown in FIGS. 3 and 4, respectively.

With reference to FIGS. 4, 6 and 8, the proximal atrial connector 126 will now be described. In this embodiment, the proximal atrial connector 126 has a proximal connector body 170 which is comprised of a square shape having a front face 171 and a plurality of side wall faces 172a–172d. The front face 171 of the connector body 170 of the proximal connector 126 includes an atrial sense contact 176. The atrial sense contact 176 is electrically connected to an atrial sense conductor 180 which extends through the proximal atrial lead body 120 to connector 116 and is connected to the sensing circuit of the control unit 104 in a manner that is known in the art. Similarly, one face 172c of the plurality of faces 172a–172d of the connector body 170 also includes an atrial pace contact 182 that is electrically connected with an atrial pace conductor 184 that extends through the proximal atrial lead body 120 to the control unit 104 (FIG. 1) and is electrically connected to the pacing pulse generation circuit (not shown) contained within the control unit 104.

As shown in FIGS. 3, 5 and 7, the distal atrial connector 130 also includes a connector body 186 which defines a plurality of faces that are adapted to receive the front face 171 and the plurality of side wall faces 172a–172d of the proximal connector 126. In this embodiment, the distal connector body 186 defines a recess or receptacle 188 that defines a front face 189 and a plurality of side wall faces 190a–190d. The recess 188 of the distal connector 130 corresponds to the connector post 170 of the proximal connector 126 such that the connector body 170 can be positioned in the recess 188 so that the faces 189, 190a–190d of the distal connector 130 are positioned adjacent the faces 171, 172a–172d, respectively, of the proximal connector 126.

In this embodiment, a plurality of conductors 196a–196e extend through the distal single-pass lead body 136 and are electrically coupled to atrial electrodes 156a–156e, respectively. A sense contact 192 is positioned on a first face 189 of the distal connector 130. In this embodiment, the most proximal atrial electrode 156e (See, FIG. 2) is preferably dedicated as the atrial sensing electrode which provides the return path for atrial stimulation pulses delivered from the electrode selected as the atrial pacing electrode in the manner that will be described in greater detail below. Accordingly, the sense contact 192 is coupled to conductor 196e. However, one of skill in the art could readily select any on the electrodes 156a–156e for the dedicated electrode, and further select the pacing as the dedicated electrode and the selectable electrode as the return or sensing electrode.

Each of the side wall faces 190a–190d of the recess 188 also includes a contact 194a–194d which is coupled to the more distal atrial electrodes 156a–156d via the conductors 196a–196d, respectively. The proximal connector 126 can be connected to the distal connector 130 in a plurality of different connection configurations. In this embodiment, the square post comprising the proximal connector post 170 can be positioned in the recess 188 defined by the distal connector 130 in four different connector configurations. Hence, the atrial pace contact 182 of the proximal connector 126 can be positioned adjacent one of the four different pacing contacts 194a–194d of the distal connector 130. The recess 188 of the distal connector 130 and the connector post 170 of the proximal connector 126 are preferably sized so that the side walls 172a–172d of the connector post 170 are positioned adjacent the side walls 190a–190d such that an electrical connection is made between the pacing contact 182 on the connector post 170 and the adjacent atrial electrode contact 194a–194d. Hence, the implanting physician can electrically connect the control unit 104 to one of the four atrial ring electrodes 156a–156d by coupling the connector 126 with the connector 130 in a desired connection configuration.

It will also be appreciated that regardless of which configuration the connector post 170 is positioned within the recess 188, the sense contact 176 on the front face 171 of the connector post 170 will always make electrical contact with the atrial sensing electrode contact 192 on the front face 189 of the recess 188 of the distal connector 126. This is the result of the sense contact 176 being geometrically centered on the front face 171 of the connector post 170 about the axis of the post and the atrial sensing electrode contact 192 being similarly centered on the front face 189 of the distal connector 126. In this way, regardless of the connection configuration, the atrial sensing electrode 156e is always coupled to the control unit 104 via the connectors 126 and 130. Hence, the implanting physician can select different atrial pacing electrodes from the group of atrial electrodes 156a–156d and still electrically connect the atrial ring electrode 156e as the return path for the stimulation pulses that will emanate from the selected atrial pacing electrode 156a–156d.

Figure 9:
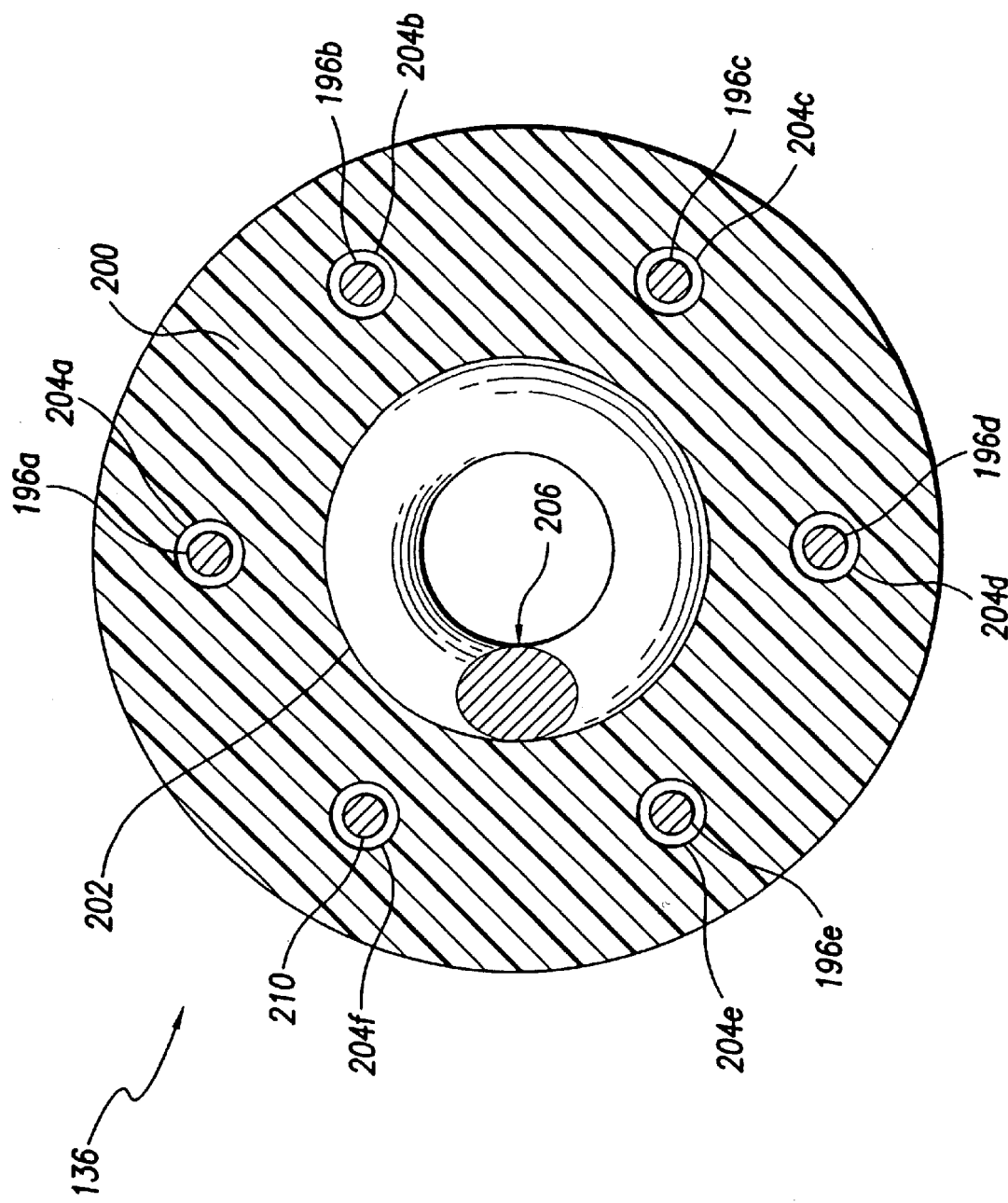
FIG. 9 is a cross-sectional view of the distal lead body of the lead assembly of FIG. 4.

Each of the conductors 196a–196e extend through the distal atrial lead body 132 to the junction 134 where they are positioned within the distal single-pass lead body 136. FIG. 9 is a cross-section of the distal single-pass lead body 136. As illustrated in FIG. 9, the single-pass lead body 136 is comprised of a tube formed of a flexible material, such as silicon rubber, that has a plurality of lumens extending the length of the lead body.

In particular, in this embodiment, the single-pass lead body 136 includes a central lumen 202 which receives a ventricular tip conductor 206 that connects the ventricular pacing tip electrode 152 to the control unit 104. The single-pass lead body 136 also includes a plurality of peripheral lumens 204a–204f that receive the atrial conductors 196a–196e and a ventricular ring conductor 210. The atrial conductors 196a–196e extend through the peripheral lumens 204a–204f into the portion 138 (FIG. 2) of the single-pass lead body 136 that is implanted within the heart wherein the conductors 196a–196e are connected to the atrial ring electrodes 156a–156e in a manner that is known in the art.

Similarly, the ventricular tip conductor 206 and the ventricular ring conductor 210 extend the length of the single-pass lead body 136 and are electrically connected to the ventricular tip electrode 152 and the ventricular ring electrode 154, respectively, in a manner that is known in the art.

Moreover, the ventricular tip conductor 206 and the ventricular ring conductor 210 also extend through the proximal ventricular lead body 124 into the control unit 104 so as to be connected to the pacing and sensing circuits contained therein in a manner known in the art.

Hence, the control unit 104 can deliver ventricular stimulation pulses between the ventricular tip electrode 152 and the ventricular ring electrode 154 to thereby provide ventricular pacing to the left ventricle of the heart. Similarly, the control unit 104 can also provide atrial stimulation pulses between the selected atrial pacing electrode 156a–156d and the dedicated atrial sensing electrode 156e through the conductors 196a–196e that extend through the peripheral lumens 204 of the single-pass lead body 136, the distal atrial lead body 132, the connectors 126 and 130, and the proximal atrial lead body 120.

Figure 10:
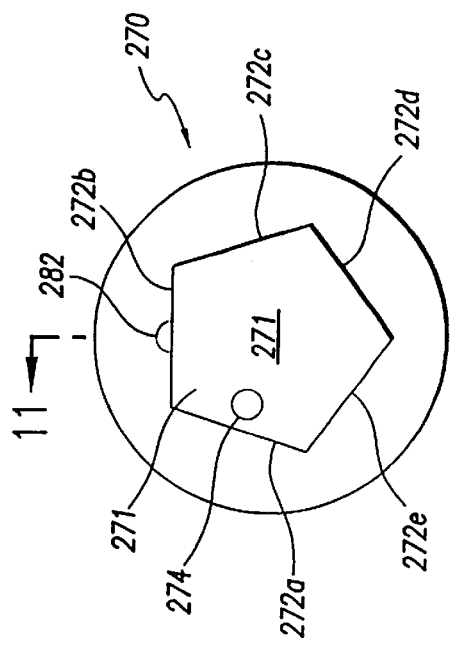
FIGS. 10 and 11 illustrate another embodiment for a proximal and distal connector, respectively, that determine which combination of electrodes will be used for pacing and sensing.
Figure 11:
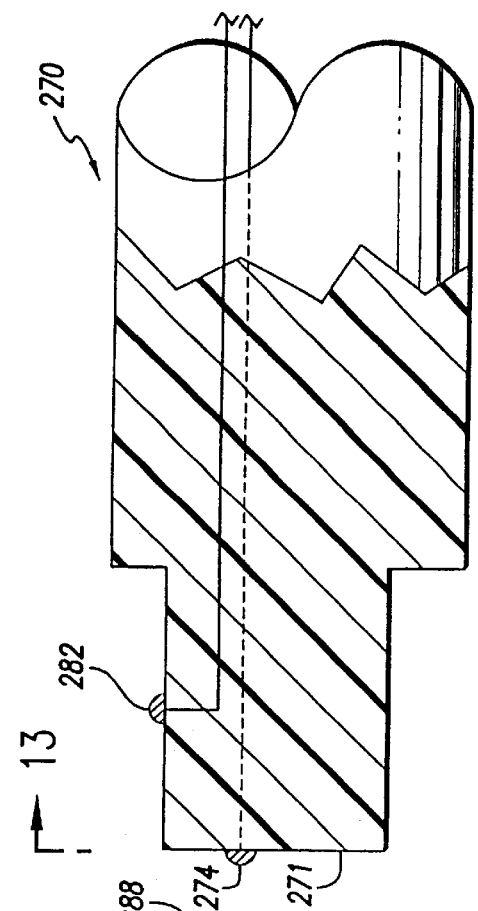
Figure 12:
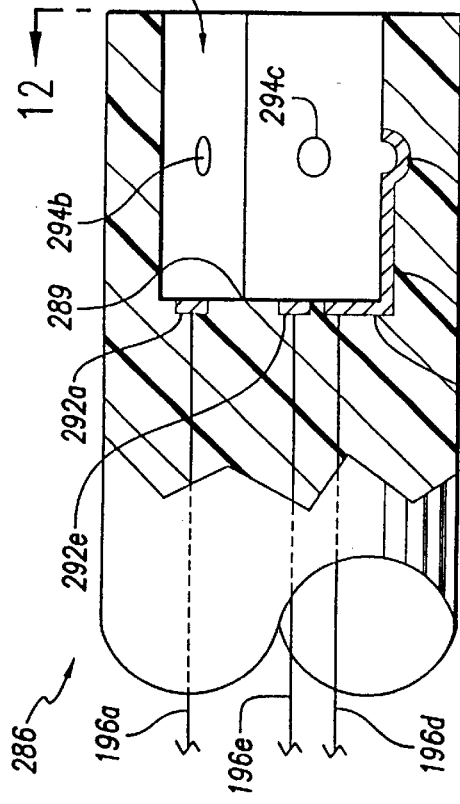
FIG. 12 is an end view of the distal connector shown in FIG. 10.
Figure 13:
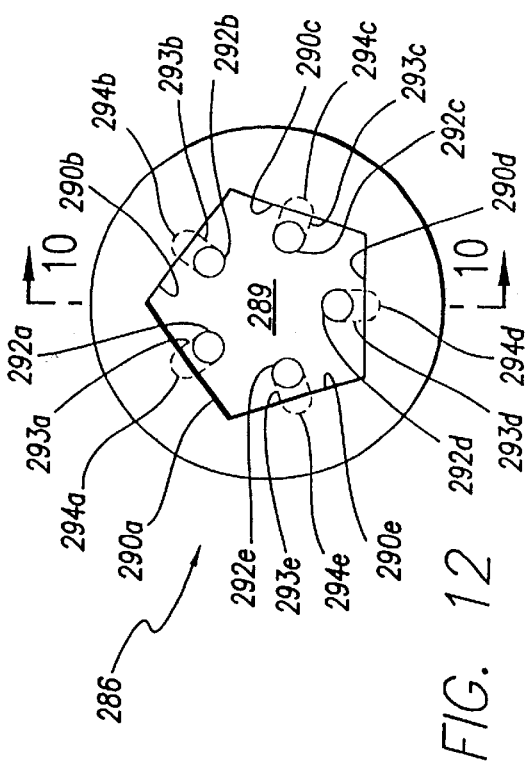
FIG. 13 is an end view of the proximal connector shown in FIG. 11.

FIGS. 10 and 11 show a cross-sectional view of a second embodiment of the distal connector 286 and the proximal connector 270, respectively, that determine which combination of electrodes will be used for pacing and sensing. FIGS. 12 and 13 illustrate an end view, and FIG. 14 illustrates an isometric view, of the distal connector 286 and the proximal connector 270 shown in FIGS. 10 and 11, respectively.

This embodiment gives the implanting physician the ability to select both the pacing atrial electrode and the sensing atrial electrode from a predetermined set of combinations of the atrial electrodes 156a–156e.

In particular, the connection 118 (FIG. 1) is comprised of a proximal connector 270 attached to the proximal atrial lead 120 and a distal connector 286 attached to the distal atrial lead 132. In this embodiment, the connectors 270 and 286 are in the configuration of a five-sided or five-faced pentagon with a front face 271.

Figure 14:
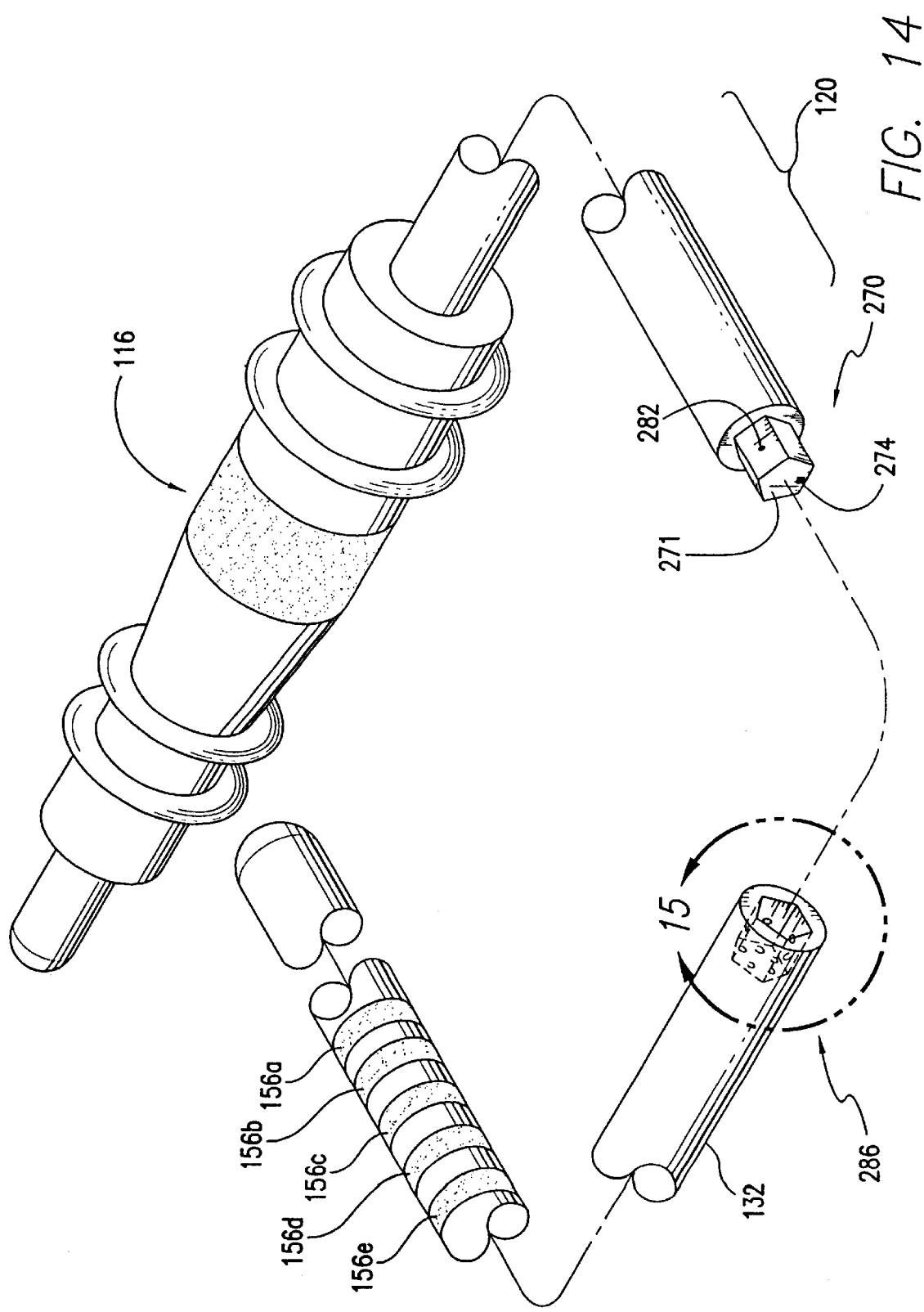
FIG. 14 is an isometric illustration of the lead assembly shown in FIGS. 10 and 11.

With reference to FIGS. 11,13 and 14, This allows six faces upon which contacts can be mounted. In this embodiment, the proximal connector 270 has a sense contact 274 positioned on the front face 271 of the proximal connector 270. The contact 274 is connected to the sensing circuit in the control unit 104 in substantially the same manner as described above. The contact 274, in this embodiment, is not centered in the front face 271, rather, it is offset so that rotation of the connector 270 about its axis results in a different spatial position of the contact 274. The connector 270 also includes a pacing contact 282 which is connected to the pacing circuit (not shown) in the control unit 104 in substantially the same manner as described above. The pacing contact 282 is positioned on one of the side wall faces 272a–272e of the proximal connector 270 in a fixed location.

Figures 15, 16:
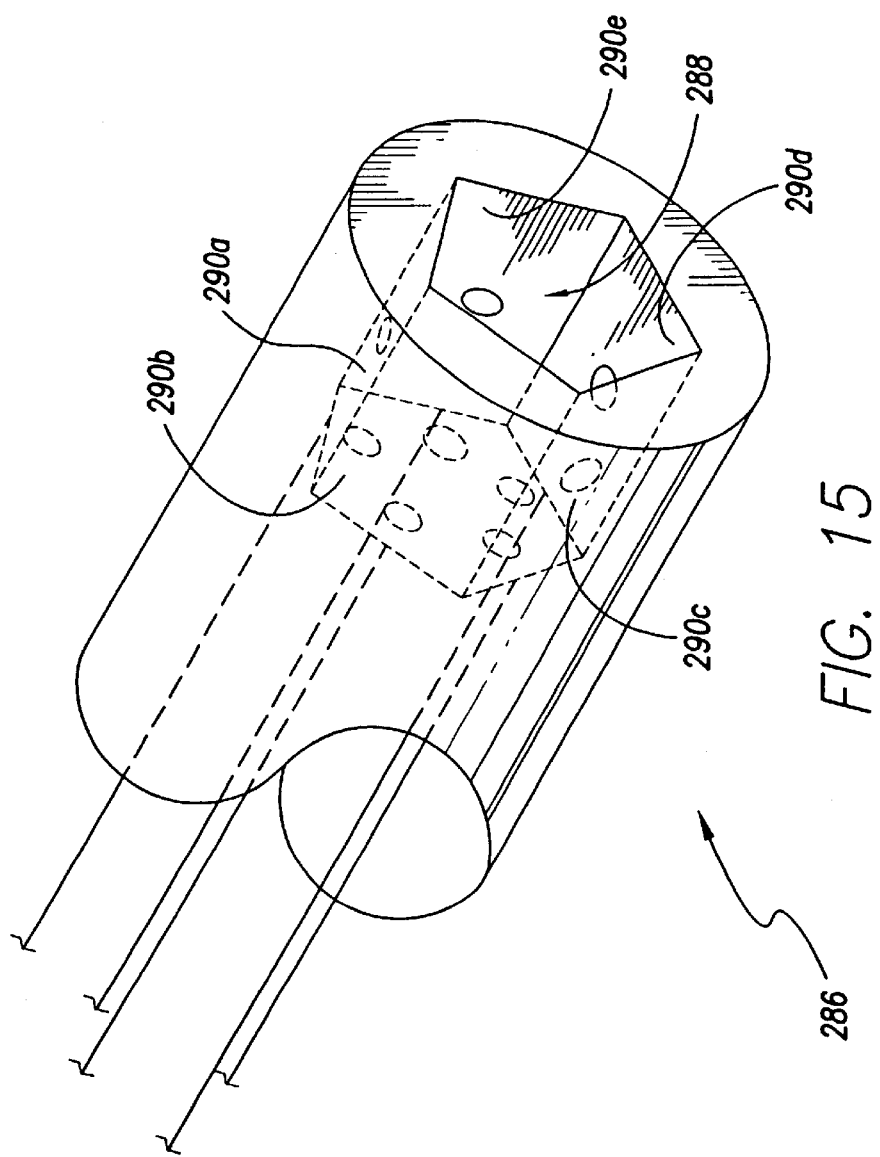
FIG. 15 is an isometric illustration of the distal connector shown in FIG. 10.
FIG. 16 is chart for selecting combinations of electrodes for pacing and sensing using the connector shown in FIGS. 10 and 11.

As best shown in FIGS. 10, 12 and 15, the distal connector 286 is comprised of a pentagon-shaped recess 288 that is adapted to receive the pentagon-shaped post comprising the connector body 270 in five different connection configurations. The recess 288 of the distal connector 286 includes a front face 289 upon which five atrial sensing electrode contacts 292a–292e are positioned. The contacts 292a–292e on the face 289 are positioned in locations such that the sense contact 274 on the front face 271 of the proximal connector 270 will make contact with one of the sensing contacts 292a–292e when the connector 270 is coupled to the connector 286 in any one of the five different connection configurations. The side walls of the recess 288 define the side walls on faces 290a–290e of the connector 286 and each of the faces 290a–290e also include an atrial pacing electrode contact 294a–294e. The pacing contacts 294a–294e are electrically connected to the atrial electrodes 156a–156e in the same manner as described above. The pacing contacts 294a–294e are also positioned so that the pace contact 282 on the connector 270 will make electrical contact with one of the atrial pacing contacts 294a–294e when the connector 270 is interconnected with the connector 286.

As best seen in FIG. 12, conductors 293a–293e electrically interconnect the atrial sensing contacts 292a–292e on the front face 289 of the connector 286 with the corresponding atrial pacing contact 294a–294e on the side walls or side faces 290a–290e of the connector 286 in the connector recess 288. The configuration of this embodiment of the connector 118 (FIG. 1) allows the treating physician to select one of the atrial electrodes 156a–156e to be an atrial pacing electrode and also select one of the atrial electrodes 156a–156e to be an atrial sensing electrode.

In particular, the connectors 270 and 286 are configured so that for each of the five different connector configurations, one of the atrial electrodes 156a–156e is selected as the sensing atrial electrode and is connected to control unit 104 via the sense contact 274 on connector 270 and a different one of the atrial electrodes 156a–156e is selected as the trial pacing electrode and is connected to the control unit 104 via the pace contact 282 on the connector 270. The table shown in FIG. 16 illustrates the possible configuration of pacing and sensing electrodes for the five different connection configurations of the connectors 270 and 286. In this embodiment, the connectors are configured so that the sensing electrode is generally positioned, for example, adjacent the pacing electrode for most of the connection configurations except with the last configuration where the atrial pacing electrode is electrode 156e and the atrial sensing electrode is electrode 156a.

In this embodiment, the implanting physician can select not only the atrial pacing electrode from the group of electrodes 156a–156e but can also select a different sensing electrode from the group of electrodes 156a–156e. This selection, in this embodiment, can be made by the implanting physician connecting the connectors 270 and 286 together in one of the connection configurations that will yield the most optimum delivery of stimulation pulses to the left atrium by the atrial electrodes 156a–156e. It will be appreciated that the configuration of the atrial pacing and atrial sensing electrode pairs can be varied by simply varying the interconnection of the conductors 293a–293e or the configuration of the connectors 270 and 286 to any of a number of possible variations within the scope of this invention.

It is contemplated that selection of atrial pacing and atrial sensing electrodes from the plurality of atrial electrodes 156a–156e, in one embodiment, will result in the sensing and pacing electrodes being positioned adjacent each other on the lead body 136. The above-discussed embodiments have also contemplated that the single-pass lead 136 would be configured for bipolar pacing. In some circumstances, it may be desirable to have unipolar pacing where one of the electrodes 156a–156e emits the therapeutic electrical stimulation and some other electrode, such as the casing of the control unit 104, functions as the return electrode. It may also be desirable to simply use one of the atrial electrodes 156a–156e as a dedicated sensing electrode or a dedicated return electrode.

To accommodate these potential situations, an alternate embodiment for the connection 118 (FIG. 1) was developed.

As shown in FIGS. 17–23, a proximal connector 370 and a distal connector 386 are six sided polygon shapes with six side walls and a front face.

Accordingly, FIGS. 17 and 18 show a cross-sectional view of a third embodiment of the distal connector 386 and the proximal connector 370, respectively. FIGS. 19 and 20 illustrate an end view, and FIG. 21 illustrates an isometric view, of the distal connector 386 and the proximal connector 370 shown in FIGS. 17 and 18, respectively.

The proximal connector 370 includes a single sense electrode 374 positioned on the front face 371 of the post, and the distal connector 386 has six atrial sensing electrodes 392a–392f positioned on the front face 389 of the recess 388. The six atrial sensing electrodes 392a–392f are positioned on the front face 389 in positions where the sense contact 374 will contact one of the six contacts 392a–392f when the proximal connector 370 is connected to the distal connector 386 in one of the six possible connection configurations. Similarly, the proximal connector 370 includes a pace contact 382 on one of the six side walls 372a–372f that will be connected to one of six atrial pacing contacts 394a–394f positioned on one of the six side walls 390a–390f of the recess 388 formed in the distal connector 386.

The pacing contact 382 and the sensing contact 374 of the proximal connector 370 are electrically connected to the control unit 104 in the above described manner.

On the distal connector 386, the six atrial sensing contacts 392a–392f are connected to the six atrial electrodes 156a–156f (FIG. 21) and six atrial pacing contacts 394a-394f are connected to the atrial electrodes 156a–156f in the above described manner.

Figures 22, 23:
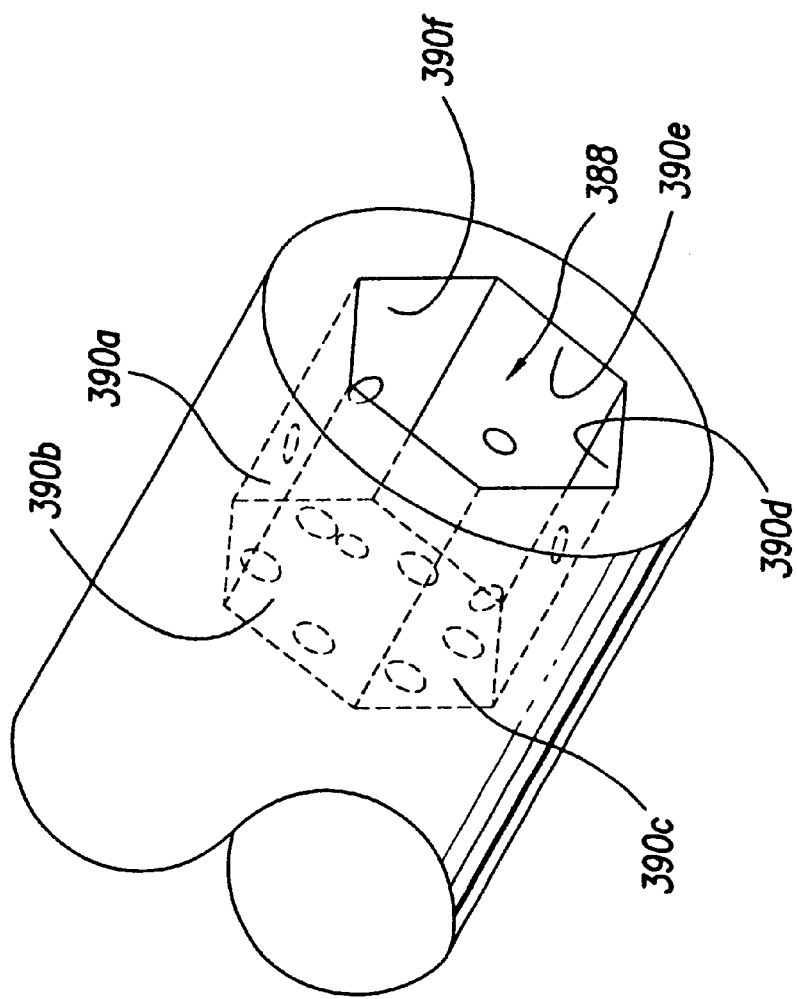
FIG. 22 is an isometric illustration of the distal connector shown in FIG. 17.
FIG. 23 is chart for selecting combinations of electrodes for pacing and sensing using the connector shown in FIGS. 17 and 18.

Hence, as is shown in the Table of FIG. 23, the implanting physician will have the ability to selectively connect either the pace contact 382 or the sense contact 374 on the proximal connector 370 to one of six combinations of the atrial electrodes 156a–156f.

Furthermore, after the physician configures the lead to connect a particular pair of electrodes (shown for example in the Table of FIG. 21) or contact to the implantable cardiac device 100, the device 100 can programmable select any combination of bipolar pacing, bipolar sensing, unipolar pacing, or unipolar sensing using any combination of the pair of electrodes and the casing.

From the foregoing, it will be appreciated that the implantable cardiac device of the above-described embodiments allows for a single-pass lead to be implanted within the coronary sinus and allows for selection by the implanting physician of one of a plurality of electrodes positioned within the coronary sinus to deliver therapeutic electrical stimulation to the heart. In the above-described embodiments, the implanting physician can select the emitting electrodes by simply configuring the connector that interconnects the single-pass lead to the control unit.

Hence, in one embodiment, dual pacing of both the left atrium and the left ventricle can be achieved by implanting a single-pass lead and then activating one of a plurality of atrial electrodes, This results in an implantable cardiac device that is more easily used in left atrium and left ventricle pacing.

Although the foregoing description of the preferred embodiments of the present invention has shown, described and pointed out the fundamental novel features of the invention, it will be understood that various omissions, substitutions and changes in the form of the detail of the apparatus as illustrated, as well as the uses thereof, may be made by those skilled in the art without departing from the spirit of the present invention. Consequently, the scope of the invention should not be limited to the foregoing discussion but should be defined by the appended claims.

What is claimed is:

1. An implantable lead adapted for use with an implantable cardiac device having pulse generating means for generating stimulation pulses to the left atrium of a patient's heart, the implantable lead comprising:

proximal coupling means, having at least one terminal, for connecting at least one electrode to the pulse generating means;

a lead body having a plurality of electrodes positioned along the lead body such that at least one of the electrodes can deliver stimulation pulses to the left atrium of the patient's heart, each of the plurality of electrodes being connected to a respective conductor; and selection means, located between the lead body and the proximal coupling means, for selectively connecting at least one of the plurality of electrodes on the lead body to the at least one terminal on the proximal coupling means.

2. The lead of claim 1, wherein the lead body further comprises:

at least one ventricular electrode, located at a distal end of the lead body, suitable for delivering stimulation pulses to the left ventricle of the patient's heart; and means for electrically interconnecting the at least one ventricular electrode with the pulse generating means.

3. The lead of claim 2, wherein the lead body comprises:

a single-pass lead body adapted to be implanted within the coronary sinus;

wherein the plurality of electrodes are spaced over a portion of the length of the single-pass lead body so as to be distributed through the coronary sinus region; and wherein the at least one ventricular electrode is positioned at a distal end of the lead body suitable for stimulating the left heart when the single-pass lead body is implanted within the patient's coronary sinus region.

4. The lead of claim 1, wherein the lead body comprises:

a plurality of lumens extending the length of the lead body; and a conductor contained within each of the plurality of lumens, each conductor being electrically connected to a respective electrode.

5. The lead of claim 1, wherein the selection means comprises:

a proximal connector having a first electrical contact coupled to the at least one terminal by a conductor; and a distal connector having a plurality of electrical contacts coupled to the plurality of electrodes by a respective conductor, and adapted for selective engagement with the proximal connector such that a plurality of combinations of electrode configurations may be selected by rotating the proximal connector before engaging the distal connector.

6. The lead of claim 5, wherein:

the proximal connector comprises a first geometric shape having a plurality of faces, wherein a first electrical contact is positioned on a first face of the plurality of faces on the proximal connector; and the distal connector has a plurality of faces corresponding to the plurality of faces on the proximal connector, the distal connector having an electrical contact respectively connected to each of the plurality of electrodes such that a different pair of the electrodes may be selected.

7. The lead of claim 6, wherein:

the distal and proximal connectors are configured so as to further define a front face on each of the connectors; and the front faces on each of the connectors are always positioned in contact with each other in each of the plurality of combinations of electrode configurations.

8. The lead of claim 7, wherein at least one of the plurality of electrodes comprises a return electrode for the delivery of stimulation pulses to the left atrium.

9. The lead of claim 8, wherein the proximal coupling means further comprises a second terminal for electrically connecting the return electrode to the pulse generating means.

10. The lead of claim 9, wherein:

the proximal connector comprises a first electrical contact positioned on a front face of the proximal connector; and the distal connector comprises a second electrical contact positioned on a front face of the distal connector so that the first electrical contact on the front face of the proximal connector mates with the first electrical contact positioned on the front face of the distal connector.

11. The lead of claim 9, wherein:

the proximal connector comprises a first electrical contact positioned on a front face of the proximal connector; and the distal connector comprises a plurality of electrical contacts positioned on a front face of the distal connector so that the first electrical contact mates with a selected one of the plurality of electrical contacts on the front face of the distal connector.

12. The lead of claim 1, wherein the lead body is configurable so that one of the plurality of electrodes can be selected as an atrial pacing electrode to deliver the stimulation pulses to the left atrium.

13. An implantable lead for use with an implantable cardiac device having a pulse generator that is configured to deliver therapeutic electrical stimulation to a patient's heart, the lead comprising:

a first lead body adapted at a proximal end for connecting an atrial pacing electrode to the pulse generator;

a second lead body having a plurality of electrodes located along the second lead body in locations wherein at least one of the plurality of electrodes is positioned within the coronary sinus region; and a connector, located between the first and second lead bodies, which is configurable so that at least one of the plurality of electrodes can be selected as the atrial pacing electrode to deliver the stimulation pulses to the left atrium.

14. The lead of claim 13, wherein the connector can be selectively connected in a plurality of configurations corresponding to the plurality of electrodes.

15. The lead of claim 14, wherein the connector comprises:

a proximal connector, electrically connected to the pulse generator, having a first shape with a plurality of faces associated therewith, wherein a pacing contact is positioned on a first face of the plurality of faces; and a distal connector, configured to engage with the proximal connector, having the first shape with a plurality of mating faces, wherein each of the plurality of mating faces includes an electrode contact that is respectively connected to one of the plurality of electrodes; and wherein the proximal connector can be coupled to the distal connector in a first of a plurality of electrode configurations which electrically connects the pacing contact of the proximal connector to a different one of the plurality of electrode contacts of the distal connector.

16. The lead of claim 14, wherein:

the first lead body is further adapted for connecting a atrial return electrode to the pulse generator;

at least one of the plurality of electrodes attached to the lead body is configured so as to provide a return electrode.

17. The lead of claim 16, wherein:

the return electrode is coupled to an electrode contact located in the center of a front face of the distal connector; and the return electrode contact on the distal connector mates to a corresponding return electrode contact located in the center of the front face of the proximal connector;

wherein the return electrode is a dedicated return electrode independent of the selected atrial pacing electrode.

18. The lead of claim 14, wherein:

the proximal connector comprises a shaped-post having a plurality of side walls and a front face; and the distal connector comprises a recess that is adapted to receive the first shaped-post, the distal connector having side walls and a front face corresponding to the shaped-post.

19. The lead of claim 14, wherein:

the proximal connector comprises a rectangular post having four side walls and a front face; and the distal connector comprises a rectangular recess having four side walls and a front face.

20. The lead of claim 14, wherein:

the proximal connector comprises a polygonal post having at least five side walls and a front face; and the distal connector comprises a polygonal recess having at least five side walls and a front face.

21. The lead of claim 13, wherein the second lead body comprises a single-pass lead body having a plurality of lumens extending the length of the single-pass lead body, each lumen having a respective conductor contained that can be used to electrically interconnect a respective electrode to the connector.

22. The lead of claim 21, further comprising:

a ventricular pacing electrode attached to the single-pass lead body at a distal end so that the ventricular pacing electrode can be positioned within the coronary sinus region so as to deliver stimulation pulses to the left ventricle of the patient's heart; and wherein the single-pass lead body is further adapted at a proximal end to connect the ventricle pacing electrode to the pulse generator.

* * * * *